United States Patent
Hoefle et al.

(12)
(10) Patent No.: US 6,900,160 B2
(45) Date of Patent: May 31, 2005

(54) TRIAZOLO-EPOTHILONES

(75) Inventors: Gerhard Hoefle, Braunschweig (DE); Nicole Glaser, Braunschweig (DE)

(73) Assignee: Gesellschaft fuer Biotechnologische Forschung mbH, Braunschweig (DE)

( * ) Notice: Subject to any disclaimer, the term of this patent is extended or adjusted under 35 U.S.C. 154(b) by 0 days.

(21) Appl. No.: 10/381,176

(22) PCT Filed: Sep. 21, 2001

(86) PCT No.: PCT/EP01/10991

§ 371 (c)(1),
(2), (4) Date: Aug. 18, 2003

(87) PCT Pub. No.: WO02/24712

PCT Pub. Date: Mar. 28, 2002

(65) Prior Publication Data
US 2004/0014982 A1 Jan. 22, 2004

(30) Foreign Application Priority Data
Sep. 22, 2000 (DE) .......................... 100 47 529
Feb. 27, 2001 (DE) .......................... 101 09 426

(51) Int. Cl.$^7$ ...................... A01N 43/78; A61K 31/429; C07D 513/02
(52) U.S. Cl. .................... 504/266; 548/154; 548/311.7; 514/368; 546/269.7; 549/429; 549/497; 549/356; 549/414

(58) Field of Search .............. 548/154, 311.7; 504/266; 514/368; 546/269.7; 5149/414, 429, 497, 356

(56) References Cited

U.S. PATENT DOCUMENTS

| | | | |
|---|---|---|---|
| 6,262,094 B1 * | 7/2001 | Hoefle et al. | 514/365 |
| 6,288,237 B1 * | 9/2001 | Hoefle et al. | 548/203 |
| 6,320,045 B1 * | 11/2001 | Kim et al. | 540/463 |
| 6,380,394 B1 * | 4/2002 | Nicolaou et al. | 548/125 |
| 6,489,314 B1 * | 12/2002 | Ashley et al. | 514/183 |

FOREIGN PATENT DOCUMENTS

| | | |
|---|---|---|
| DE | 41 38 042 A | 5/1993 |
| DE | 199 07 588 A | 8/2000 |
| EP | 0 625 520 A | 11/1994 |
| WO | WO 00/50423 A | 8/2000 |

OTHER PUBLICATIONS

Nicolaou, K.C.; Roschangar, Frank; Vourloumis, Dionisios: "Chemical Biology of Epothilones". *Angew. Chem. Int. Ed.* 1998, 37, pp. 2014–2045.

* cited by examiner

Primary Examiner—Golam M M Shameem
(74) Attorney, Agent, or Firm—Frommer Lawrence & Haug LLP; Ronald R. Santucci

(57) ABSTRACT

The invention relates to triazolo-thiazole analogues of epothilone A and epothilone B.

5 Claims, 4 Drawing Sheets

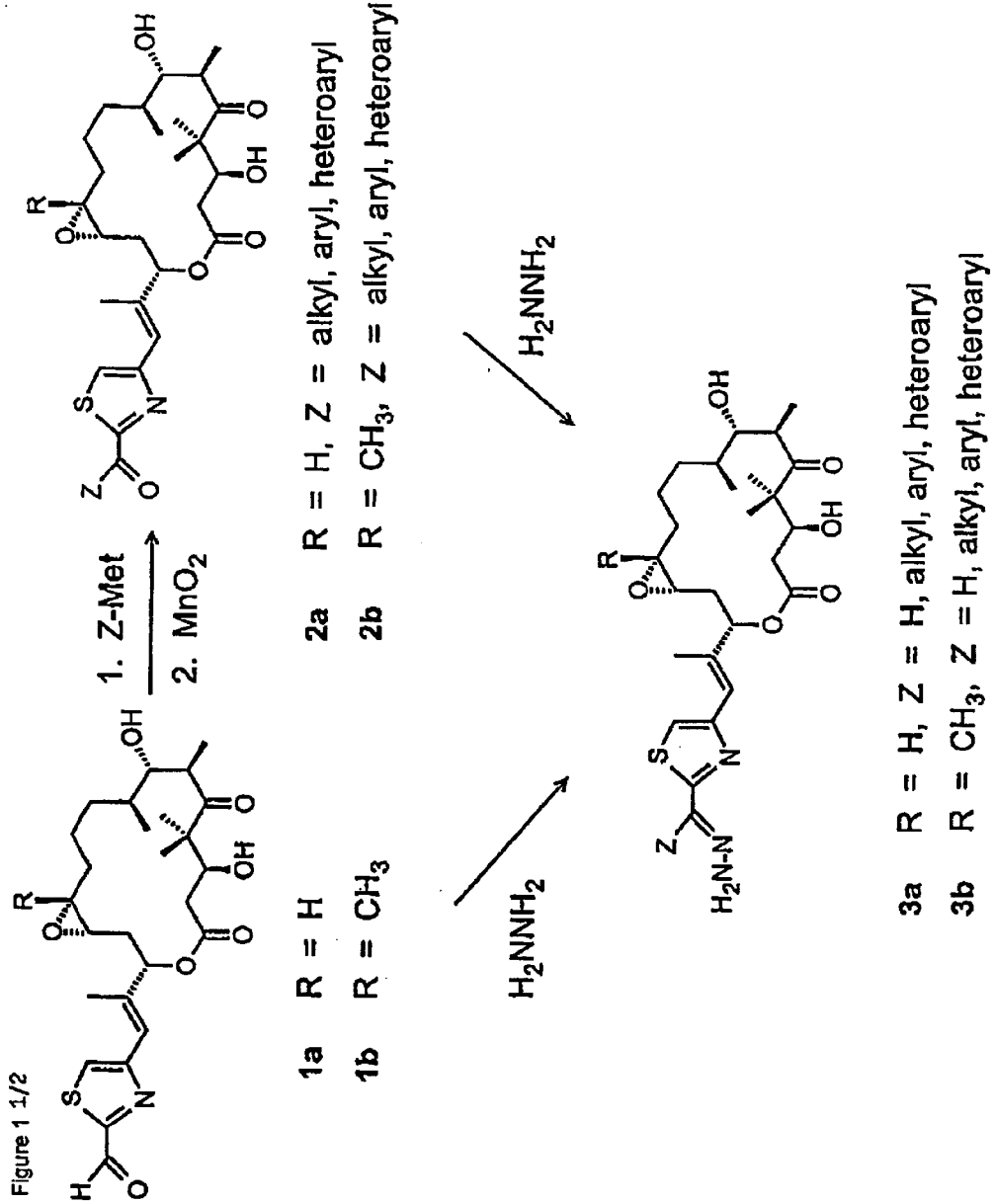
Figure 1 1/2

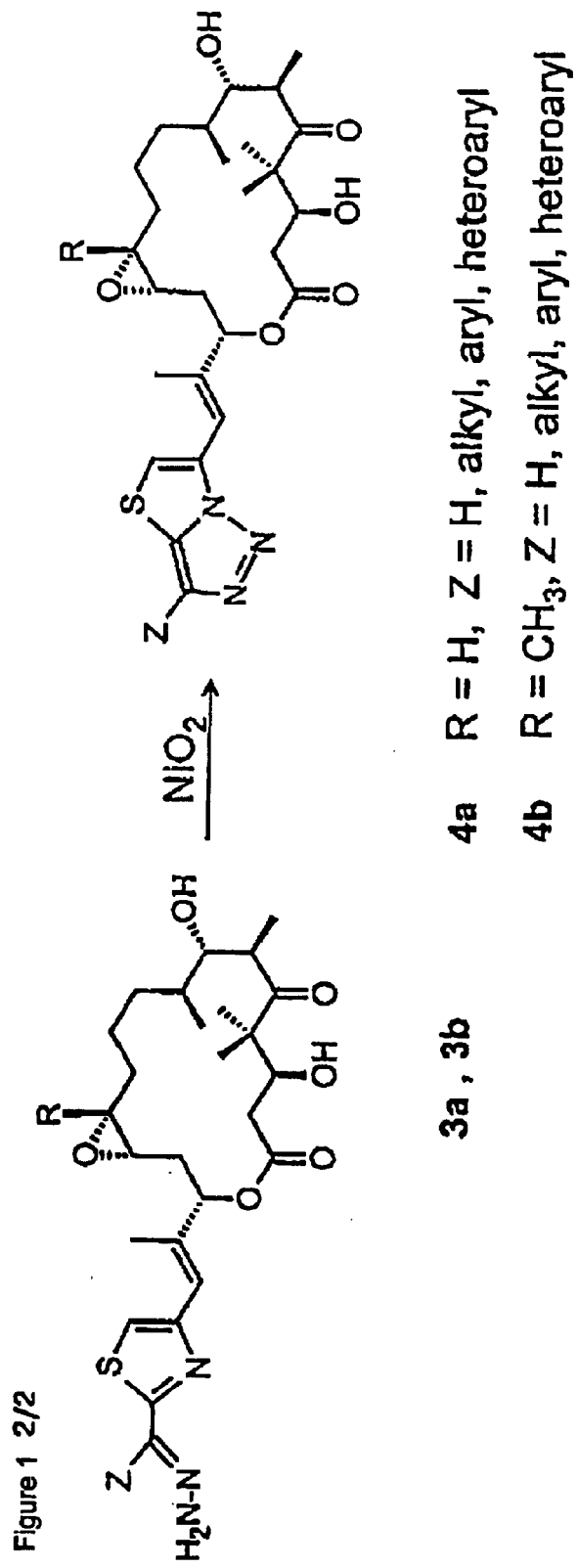
Figure 1 2/2

Figure 3
Abb. C
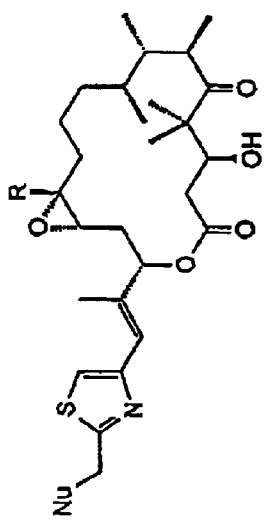
4a R = H
4b R = CH$_3$
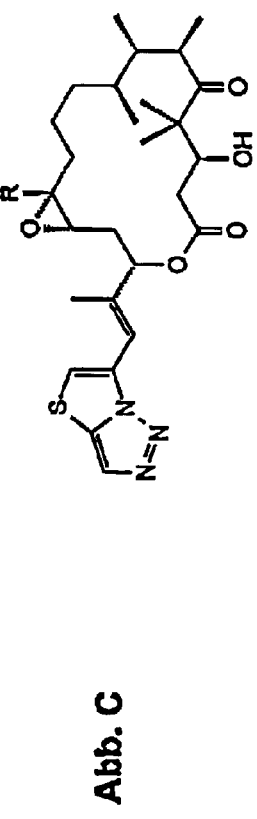
5a R = H
5b R = CH$_3$
Abb. D
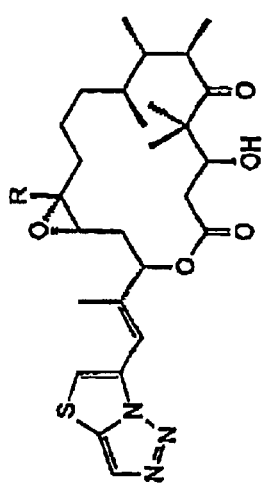
6a R = H
6b R = CH$_3$

TRIAZOLO-EPOTHILONES

This application is a 371 of PCT/EP01/10991 filed on Sep. 21, 2001, published on Mar. 28, 2002 under publication number WO 02/24712 A1 which claims priority benefits from German patent application numbers DE 100 47 529.9 filed Sep. 22, 2000 and DE 101 09 426.4 filed Feb. 27, 2001.

The invention relates to triazolo-thiazole analogues of epothilone A and epothilone B.

Epothilones are macrocyclic lactones having a fungicidal and cytotoxic effect. There is a continuous need for analogues or derivatives having comparable or better activity, which can be used as fungicides or cytostatic agents.

An overview of the chemistry of epothilones is given, for example, by Nicolaou et al. in Angew. Chem. Int. Ed. 1998, Vol. 37, 2014–2045.

The problem of the invention is to provide epothilone analogues or derivatives of that kind.

The invention accordingly relates to triazolo-thiazole analogues of epothilone A and epothilone B of formula 4a or 4b:

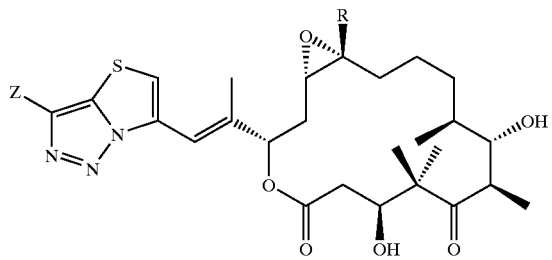

4a R=H, Z=H, alkyl, aryl. heteroaryl
4b R=CH$_3$, Z=H, alkyl, aryl. heteroaryl
wherein:
R denotes H, CH$_3$
Z denotes H, alkyl, aryl, heteroaryl.

The triazolo-thiazole epothilones according to the invention are very effective fungicides and highly potent cytostatic agents having favourable pharmacological properties.

Alkyl denotes straight-chain or branched C$_1$–C$_6$alkyl which may be (mono- or poly-)substituted as desired, for example methyl, ethyl, propyl, butyl, isobutyl, tert-butyl, pentyl and hexyl. Examples of substituents are C$_1$–C$_6$alkoxy, C$_1$–C$_6$acyl, hydroxyl and halogen such as bromine, chlorine, fluorine and iodine.

Aryl denotes mononuclear or polynuclear aromatic systems which may be (mono- or poly-)substituted as desired, for example phenyl, o-, m-, p-tolyl, o-, m-, p-xylyl, benzyl, phenethyl and naphthyl. Examples of substituents are C$_1$–C$_6$alkyl, C$_1$–C$_6$alkoxy, C$_1$–C$_6$acyl, hydroxyl and halogen such as bromine, chlorine, fluorine and iodine.

Heteroaryl denotes mononuclear or polynuclear heteroaromatic systems which may be (mono- or poly-) substituted as desired, it being possible for the aromatic nucleus to have one or more hetero atoms selected from N, O and S. Examples of heteroaryl are furyl, pyranyl, pyrrolyl, imidazolyl, pyrazolyl, pyridyl and indolyl. Examples of substituents are C$_1$–C$_6$alkyl, C$_1$–C$_6$alkoxy, C$_1$–C$_6$acyl, hydroxyl and halogen such as bromine, chlorine, fluorine and iodine.

The invention relates also to a method of preparing the triazolo-thiazole analogues of epothilone A and epothilone B according to the invention and to fungicidal and pharmaceutical compositions comprising one or more such analogues, and to the use of the analogues and of the fungicidal or pharmaceutical compositions comprising them for combating fungi or for treating diseases that can be treated with cytostatic agents, for example tumour diseases such as cancer or disorders of cell growth.

The fungicidal and pharmaceutical compositions may comprise, besides the actual active ingredient, conventional carriers, diluents or excipients, for example stabilisers such as UV absorbers, anti-oxidants and preservatives.

BRIEF DESCRIPTION OF THE DRAWINGS

FIG. 1 is a synthesis route for preparation of the triazolo-thiazole analogues of epothilone A, and epothilone B according to the invention.

FIG. 3 is another synthesis route for preparation of the analogues of the present invention.

Figure 2:
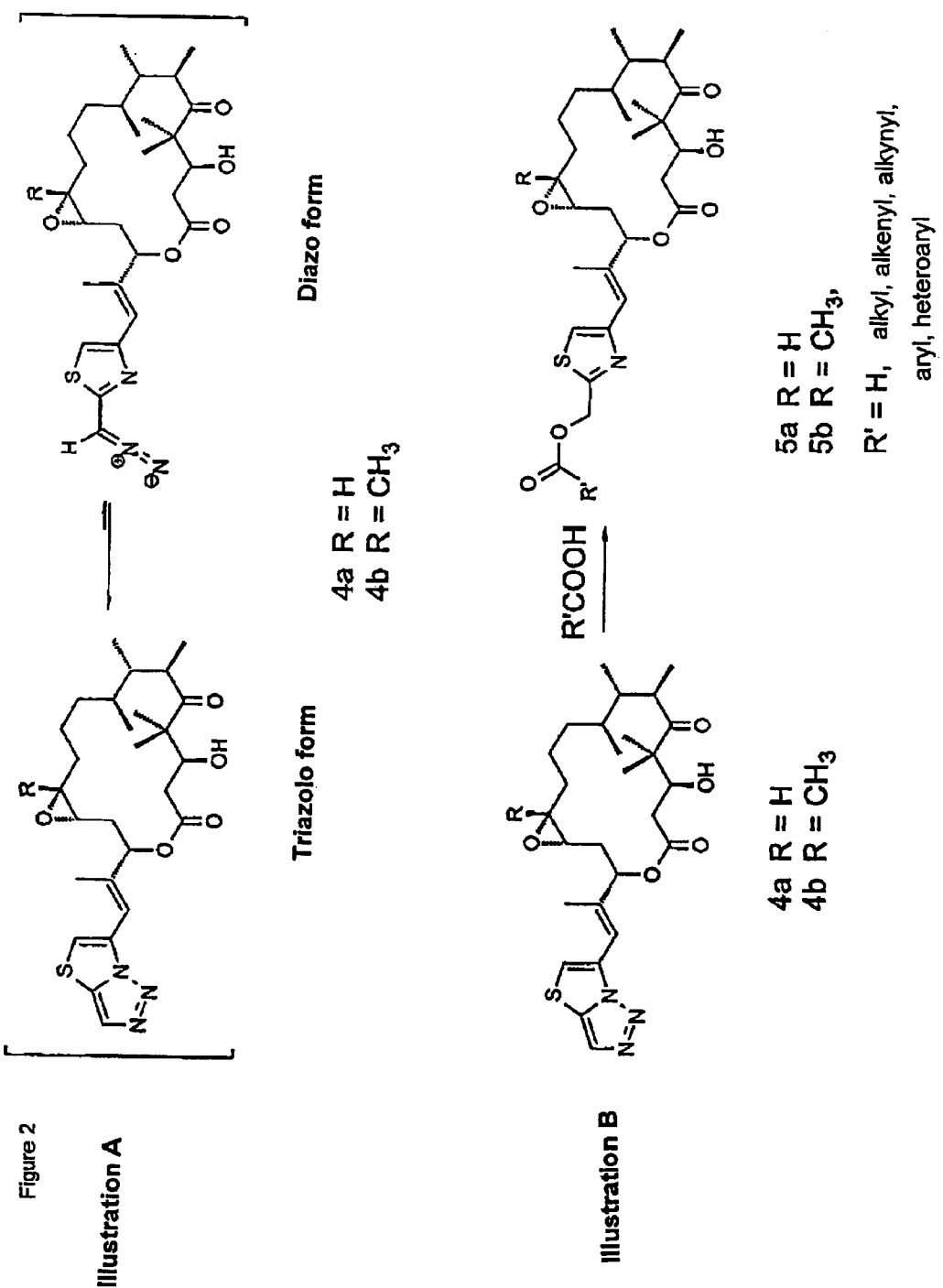
FIG. 2 is a synthesis route for preparation of the diazo from the triazolo form according to the invention.

The preparation of the triazolo-thiazole analogues of epothilone A and epothilone B according to the invention is described hereinbelow, without limitation, with reference to FIG. 1. The abbreviation Met denotes metal.

The preparation of C21-modified epothilones, that is to say the aldehydes, ketones and hydrazones of formulae 1, 2 and 3, respectively, is described in the published German Patent Application DE 199 07 588 and in the published International Patent Application WO 2000/050423 of the Applicant. In the method according to the invention, oxidative ring closure is performed on the hydrazone derivatives of formulae 3a and 3b with the aid of metal oxides, preferably NiO$_2$, K$_3$[Fe(CN)$_6$], lead tetraacetate or sodium hypochloride (cf. Houben-Weyl, Vol. E 14b, 4th Edition, 1999).

Synthesis of a triazolo-thiazole analogue of epothilone A (formula 4a, Z=H):

24.6 mg (47.2 μmol) of epothilone-A-21-aldehyde hydrazone (formula 3a) are dissolved in 1.5 ml of absolute dichloromethane. Three aliquots, each of 42.8 mg (472.2 μmol), of nickel peroxide are added at 15-minute intervals, with stirring at room temperature. The mixture is then filtered over Celite, rinsing with dichloromethane. The combined organic phases are concentrated and are dried in a high vacuum. The crude product is purified by means of preparative HPLC (mobile phase: acetonitrile/water 38:62; column: Nucleosil 100 C18 7 μm, 21×250 mm). 12.0 mg (49%) of product were obtained.

The spectroscopic data are identical to epothilone A (cf. DE 4138042 C2) with the exception of:

$^1$H NMR (400 MHz, CDCl$_3$): d=2.25 (dt, 2a-H), 2.57 (dd, 2b-H), 4.63 (m, 3-H), 5.02 (dd, 3-OH), 1.68 (m, 14a-H), 2.31 (dt, 14b-H), 5.53 (d, 15-H), 6.92 (bs, 17-H), 7.06 (s, 19-H), 7.84 (s, 21-H), 1.08 (s, 22-H), 1.55 (s, 23-H); $^{13}$C NMR (100 MHz, CDCl$_3$): d=73.0 (3-C), 54.7 (4-C), 41.4 (6-C), 71.4 (7-C), 32.0 (14-C), 74.9 (15-C), 145.1 (16-C), 109.2 (17-C), 129.2 (18-C), 115.5 (19-C), 136.4 (20-C), 124.8 (21-C), 15.9 (C-22), 23.3 (23-C), 12.7 (24-.C), 18.1 (27-C); HRMS (DCI): C$_{26}$H$_{37}$N$_3$O$_6$S: [M+NH$_4$+] calculated 537.2747, found 537.2721.

Synthesis of a triazolo-thiazole analogue of epothilone B (formula 4b, Z=H):

8.1 mg (15.1 μmol) of epothilone-B-21-aldehyde hydrazone (formula 3b) are dissolved in 1 ml of absolute dichloromethane. 13.7 mg (151.4 μmol) of nickel peroxide are added to the solution, whereupon stirring is carried out at room temperature for 15 minutes. The nickel peroxide is filtered off over Celite, washing with dichloromethane. The combined organic phases are concentrated and are dried in a high vacuum. The crude product is purified by means of preparative HPLC (mobile phase: acetonitrile/water 40:60; column: Nucleosil 100 C18 7 μm, 21×250 mm), yielding 4.7 mg (58%) of product.

The spectroscopic data are identical to epothilone B (cf. DE 4138042 C2) with the exception of:

$^1$H NMR (400 MHz, CDCl$_3$): d=2.25 (dt, 2a-H), 2.59 (dd, 2b-H), 4.69 (m, 3-H), 5.02 (dd, 3-OH), 1.76 (m, 14a-H), 2.31 (dt, 14b-H), 5.53 (d, 15-H), 6.91 (bs, 17-H), 7.06 (s, 19-H), 7.85 (s, 21-H), 1.08 (s, 22-H), 1.56 (s, 23-H); $^{13}$C NMR (100 MHz, CDCl$_3$): d=71.3 (3-C), 54.9 (4-C), 41.0 (6-C), 72.4 (7-C), 33.1 (14-C), 75.2 (15-C), 145.3 (16-C), 108.9 (17-C), 129.2 (18-C), 115.5 (19-C), 136.5 (20-C), 124.9 (21-C), 15.7 (22-C), 23.2 (23-C), 12.0 (24-C), 18.1 (27-C); MS (ESI): [M+H$^+$]=534.

The pharmacological activity is shown in the following Table:

Growth Test Using Mammalian Cell Cultures

| Cell line | Origin | Triazolo derivative of | |
| --- | --- | --- | --- |
| | | epothilone A IC-50 [ng/ml] | epothilone B |
| L929 | Mouse (subcutaneous fat tissue) | 10 | 1.0 |
| K-562 | Human (leukaemia) | 6 | 0.7 |
| U-937 | Human (lymphoma) | 4 | 0.5 |

Preparation of 21-O-acetyl-epothilon E (5a, R'=CH$_3$):

2 μl (35.0 μmol) of glacial acetic acid are added to a solution of 3.2 mg (6.2 μmol) of triazolo-epothilone A in 250 μl of dichloromethane and stirring is carried out overnight at room temperature. Water is added to the reaction mixture and extraction with ethyl acetate is carried out three times. The combined organic phases are concentrated and are dried in a high vacuum. 2.8 mg (82%) of 21-O-acetyl-epothilone E were obtained.

The spectroscopic data are identical to epothilone A (cf. DE 4138042 C2) with the exception of:

$^1$H NMR (400 MHz, CDCl$_3$): δ=6.60 (bs, 17-H), 7.14 (s, 19-H), 5.34 (s, 21-H$_2$), 2.14(s, 2'-H$_3$); $^{13}$C NMR (100 MHZ, CDCl$_3$): 137.8 (C-16), 119.6 (C-17), 152.2 (C-18), 118.0 (C-19), 163.7 (C-20), 62.5 (C-21), 170.2 (C-1'), 20.9 (C-2'); R$_f$ (CH$_2$Cl$_2$/MeOH 95/5): 0.45; HRMS (EI) C$_{28}$H$_{41}$NO$_8$S: [M]$^+$ calculated 551.2553, found 551.2519

Preparation of epothilone E-21-O-(3'-methoxycarbonyl)propynoic acid ester (5a, R'=CH$_3$OOC—C$_2$):

7.0 mg (55.0 μmol) of acetylenedicarboxylic acid monomethyl ester are added to a solution of 5.1 mg (9.8 μmol) of triazolo-epothilone A in 400 μl of dichloromethane. The reaction mixture is stirred overnight at room temperature, water is then added thereto, and extraction with ethyl acetate is carried out three times. The combined organic phases are concentrated and are dried in a high vacuum. After purification by means of PLC (CH$_2$Cl$_2$/methanol 95/5) 3.6 mg (59%) of epothilone E-21-O-(3'-methoxycarbonyl)propynoic acid ester were obtained.

The spectroscopic data are identical to epothilone A (cf. DE 4138042 C2) with the exception of:

$^1$H NMR (400 MHz, CDCl$_3$): δ=5.45 (dd, 15-H), 6.60 (17-H), 7.20 (s, 19-H), 5.49 (bs, 21-H$_2$), 3.85 (s, 5'-H$_3$); $^{13}$C NMR (100 MHz, CDCl$_3$): 76.5 (C-15), 138.2 (C-16), 119.5 (C-17), 153.0 (C-18), 118.8 (C-19), 161.2 (C-20), 64.2 (C-21), 151.1 (C-1'), 152.0 (C4'), 53.6 (C-5'); R$_f$ (CH$_2$Cl$_2$/MeOH 95/5): 0.32; MS (DCl): [M+NH$_4$]$^+$=637.

Photolysis of triazolo-epothilone A to form 21-O-methyl-epothilone A (5a, Nu-H=CH$_3$OH):

9.7 mg (18.7 μmol) of triazolo-epothilone A are dissolved in 1 ml of methanol and, with cooling (ice bath 0° C.), are exposed to light for four hours using a mercury vapour lamp (DEMA, HPK-125). The solvent is then reduced and the reaction mixture is separated by means of preparative HPLC (CH$_3$CN/H$_2$O 40/60). 2.1 mg (24%) of 21-methoxy-epothilone A were isolated.

The spectroscopic data are identical to epothilone A (cf. DE 4138042 C2) with the exception of:

$^1$H NMR (300 MHz, CDCl$_3$): δ=6.61 (bs, 17-H), 7.13 (s, 19-H), 4.71 (s, 21-H$_2$), 3.49 (s, 1'-H$_3$); $^{13}$C NMR (75 MHz, CDCl$_3$): 137.5 (C-16), 120.0 (C-17), 152.2 (C-18), 117.3 (C-19), 167.8 (C-20), 71.5 (C-21), 59.1 (C-1'); R$_f$ (CH$_2$Cl$_2$/MeOH 95/5): 0.33; HRMS (El): C$_{27}$H$_{41}$NO$_7$S: [M]$^+$ calculated 523.2604, found 523.2609.

1,3-Dipolar cycloaddition of acetylenedicarboxylic acid dimethyl ester and triazolo-epothilone A to form the pyrazole derivative 6Ha:

1.8 mg (3.5 μmol) of triazolo-epothilone A are dissolved in 200 μl of dichloromethane. Over a period of four hours, three aliquots, each of 4.3 μl (34.7 μmol), of acetylenedicarboxylic acid dimethyl ester are added and stirred at room temperature. The reaction mixture is concentrated slightly and separated by means of PLC (CH$_2$Cl$_2$/methanol 95/5). 2.0 mg (87%) of cycloaddition product were obtained.

The spectroscopic data are identical to epothilone A (cf. DE 4138042 C2) with the exception of:

$^1$H NMR (400 MHz, CDCl$_3$): δ=5.49 (dd, 15-H), 6.63 (bs, 17-H), 7.29 (s, 19-H), (s, 4'-H$_3$), 3.95 (s, 6'-H$_3$); R$_f$ (CH$_2$Cl$_2$/MeOH 95/5): 0.17; HRMS (DCl): C$_{32}$H$_{43}$N$_3$O$_{10}$S: [M+H]$^+$ calculated 662.2742, found 662.2778.

What is claimed is:

1. Triazolo-thiazole analogues of epothilone A and epothilone B of formula 4a or 4b:

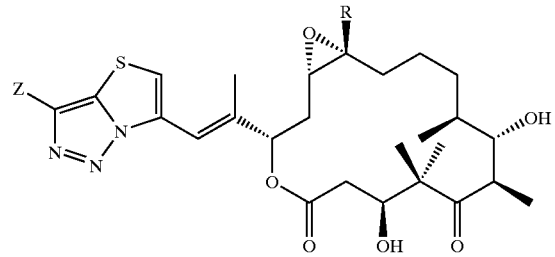

4a R=H, Z=H, alkyl, aryl, heteroaryl
4b R=CH$_3$, Z=H, alkyl, aryl, heteroaryl wherein:
R denotes H or CH$_3$
Z denotes h, alkyl, aryl or heteroaryl.

2. Triazolo-thiazole analogues of epothilone A and epothilone B according to claim 1, wherein:
alkyl denotes straight-chain or branched C$_1$–C$_6$alkyl, which may be (mono- or poly-)substituted as desired, and/or
aryl denotes mononuclear or polynuclear aromatic systems, which may be (mono- or poly-)substituted as desired, and/or heteroaryl denotes mononuclear or polynuclear heteroaromatic systems, which may be (mono- or poly-) substituted as desired.

3. Triazolo-thiazole analogues of epothilone A and epothilone B according to claim 2, wherein:

alkyl denotes methyl, ethyl, propyl, isopropyl, butyl, isobutyl, tert-butyl, pentyl or hexyl, optionally substituted by $C_1$–$C_6$alkoxy, $C_1$–$C_6$acyl, hydroxyl or halogen, especially Br, Cl, F or I, and/or aryl denotes phenyl, o-, m-, p-tolyl, o-, m-, p-xylyl, benzyl, phenethyl or naphthyl, optionally substituted by $C_1$–$C_6$alkyl, $C_1$–$C_6$alkoxy, $C_1$–$C_6$acyl, hydroxyl or halogen, especially Br, Cl, F or I, and/or heteroaryl denotes furyl, pyranyl, pyrrolyl, imidazolyl, pyrazolyl, pyridyl or indolyl, optionally substituted by $C_1$–$C_6$alkyl, $C_1$–$C_6$alkoxy, $C_1$–$C_6$acyl, hydroxyl or halogen, especially Br, Cl, F or I.

4. A pharmaceutical composition comprising or consisting of one or more triazolo-thiazole analogues of epothilone A or epothilone B according to one of claims 1 to 3 together with a pharmaceutically acceptable carrier, diluent or excipient.

5. A fungicidal composition comprising or consisting of one or more triazolo-thiazole analogues of epothilone A or epothilone B according to one of claims 1 to 3 together with a carrier, diluent or excipient that is acceptable for fungicides.

* * * * *